US010438693B1

(12) United States Patent
Vandervoort et al.

(10) Patent No.: US 10,438,693 B1
(45) Date of Patent: Oct. 8, 2019

(54) METHODS AND SYSTEMS FOR CLAIM ADJUDICATION

(75) Inventors: John William Vandervoort, O'Fallon, IL (US); Heather D. Sundar, Edwardsville, IL (US); Michael Z. Chen, St. Louis, MO (US); Adam W. Kautzner, Festus, MO (US); Randy L. Canis, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 1009 days.

(21) Appl. No.: 13/338,890

(22) Filed: Dec. 28, 2011

(51) Int. Cl.
  *G16H 20/60* (2018.01)
  *G06Q 40/08* (2012.01)
  *G16H 10/60* (2018.01)

(52) U.S. Cl.
  CPC ............ *G16H 20/60* (2018.01); *G06Q 40/08* (2013.01); *G16H 10/60* (2018.01)

(58) Field of Classification Search
  CPC ........ G06Q 50/22; G06Q 50/24; G06Q 40/08; G16H 20/60; G16H 10/60
  See application file for complete search history.

(56) References Cited

U.S. PATENT DOCUMENTS

| | | | | |
|---|---|---|---|---|
| 7,440,904 | B2* | 10/2008 | Hasan | G06F 19/322 705/2 |
| 7,469,215 | B2* | 12/2008 | Kwan | G01C 21/34 705/37 |
| 8,036,913 | B1 | 10/2011 | Pinsonneault et al. | |
| 8,447,628 | B2* | 5/2013 | Kalies, Jr. | 705/2 |
| 8,781,851 | B2* | 7/2014 | Anderson et al. | 705/2 |
| 2002/0032582 | A1* | 3/2002 | Feeney, Jr. | G06F 19/3462 705/2 |
| 2008/0126131 | A1* | 5/2008 | Lou | G06Q 50/24 705/3 |

OTHER PUBLICATIONS

Brase, Twila, "National Patient ID", Jul. 2012, Policy Insights Government Health Surveillance vol. 1.*
MedImpact International, "Harnessing the Potential of Pharmacy Benefit Management (PBM)," 1st Annual Pharmacoeconomics Middle East Forum, Mar. 4, 2011, pp. 1-18.
"Systems Xcellence Introduces New Product for Pre and Post Adjudication Software for Pharmacies and Managed Care Organizations," http://findarticles.com/p/articles/mi_mOEIN/is_2000_March_14/ai_60080890/ Mar. 14, 2000, pp. 1-4.

(Continued)

*Primary Examiner* — Eliza A Lam
(74) *Attorney, Agent, or Firm* — Husch Blackwell LLP (57) ABSTRACT

Methods and systems for claim adjudication are described. In one embodiment, a status of a drug benefit plan associated with a member is determined. Claims data associated with the member is accessed. A current-filled prescription is identified based on the claims data. At least one adjudication operation for the current-filled prescription is performed prior to receiving a new request for the current-filled prescription. The new request is determined as fillable based on the performance of the at least one adjudication operation. A notification is generated to the member based on the determination. Additional methods and systems are disclosed.

19 Claims, 6 Drawing Sheets

(56) References Cited

OTHER PUBLICATIONS

"RelayHealth Puts HIPAA 5010, ICD-10 Compliance Tools in the Cloud," http:www.icd10watch.com/blog/relayhealth-puts-hipaa-5010-icd-10-compliance-tools-cloud/, Nov. 10, 2010, pp. 1-2.

"Emdeon Clinical Integrity for Claims," http://www.emdeon.com/clinicalintegrity/ downloaded May 31, 2012, pp. 1-2.

Young Etheridge, "PKI How and Why It Works—Technology Information," http://findarticles.com/p/articles/mi_m0DUD/is_1_22/ai_68863992/ Jan. 2001, pp. 1-6.

"Pharmacy Dispensing," http://www.firstdatabank.com/Markets/pharmacy-dispensing.aspx, downloaded May 31, 2012, pp. 1-2.

\* cited by examiner

METHODS AND SYSTEMS FOR CLAIM ADJUDICATION

FIELD

The field relates to claim adjudication, and more particularly to the adjudication of prescription drug claims.

BACKGROUND

Pharmacy benefit managers (PBMs) may offer a benefit plan design that includes a prescription drug benefit. Claim adjudication, in the context of a prescription drug benefit, refers to the determination of the payment or financial responsibility of a claim for the prescription drug after the prescription drug benefit of the member is applied to the prescription drug claim.

DETAILED DESCRIPTION

Example methods and systems for claim adjudication are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a client engages a PBM to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services. In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then may adjudicate the claim associated with the prescription drug and provides a response to the pharmacy following performance of the aforementioned functions. As part of the adjudication, the client (or the PBM on behalf of the client) may ultimately reimburse the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

Figure 1:
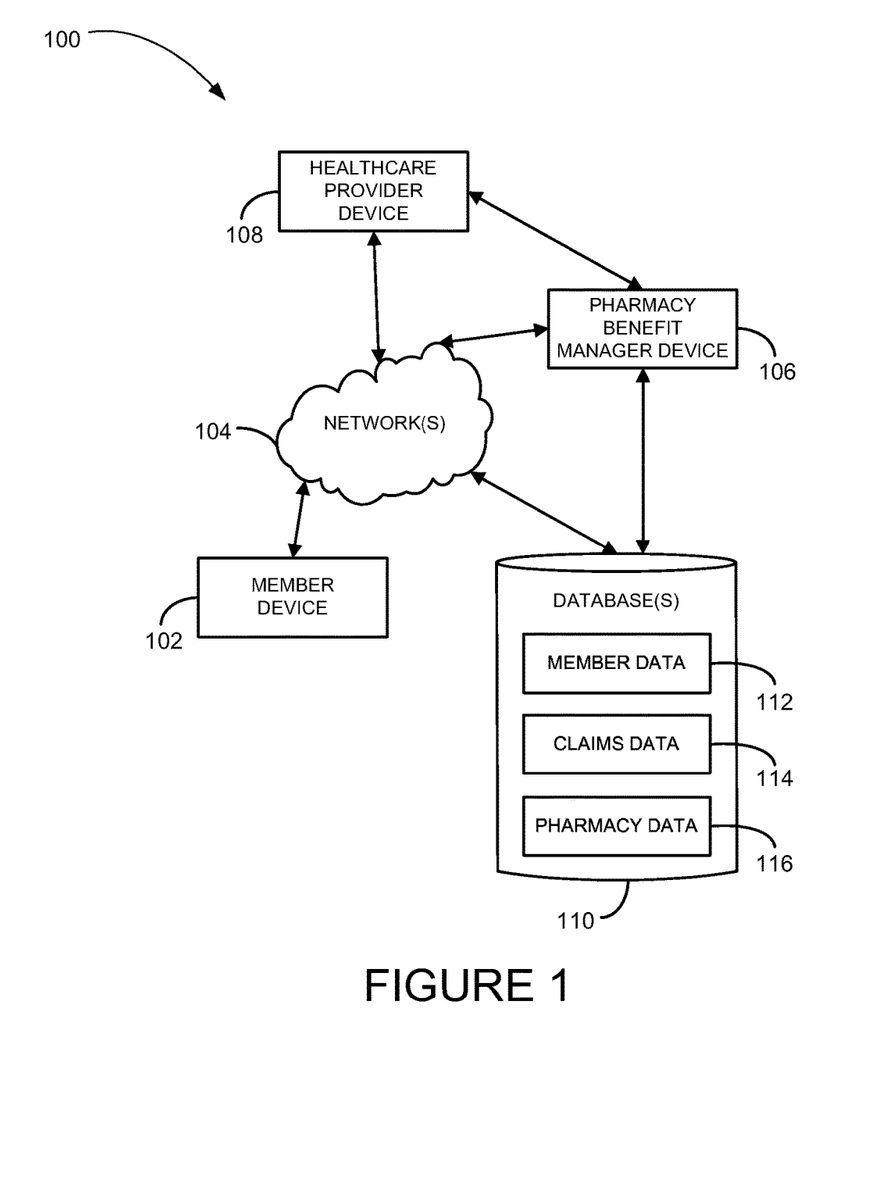
FIG. 1 is a block diagram of an example system, according to an example embodiment.

FIG. 1 is a block diagram of an example system 100, according to an example embodiment. The system 100 includes a member device 102 in communication with a pharmacy benefit manager device 106 over a network 104. The pharmacy benefit manager device 106 may be in communication with a healthcare provider device 108 over a network 104.

The member device 102 may be used by a device operator. The device operator may be a member that is either a participant in a drug benefit plan or a beneficiary of the participant (e.g., a spouse or a child of the beneficiary). However, the device operator may be another person operating the member device 102 on behalf of the member. Examples of such other people include parents, guardians and caregivers.

The member device 102 is used by a device operator. The member device 102 may be a stand-alone device that solely provides at least some of the functionality to enable the claim adjudication for prescription drugs, or may be a multi-use device that has functionality outside of claim adjudication as described herein. Examples of the member device 102 include a set-top box (STB), a receiver card, a mobile telephone, a personal digital assistant (PDA), a display device, a portable gaming unit, and a computing system; however, other devices may also be used. For example, the member device 102 may include a mobile electronic device, such an IPHONE or IPAD device by Apple, Inc., mobile electronic devices powered by ANDROID by Google, Inc., and a BLACKBERRY device by Research In Motion Limited. The member device 102 also include other computing devices, such as desktop computing devices, notebook computing devices, netbook computing devices, gaming devices, and the like. Other types of electronic devices may also be used.

The network 104 by which the member device 102 communicates with the pharmacy benefits manager device 106 and the healthcare provider device 108 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a Wi-Fi network, or an IEEE 802.11 standards network, as well as various combinations thereof. Network 104 may also include optical communications. Network 104 may also include wired communication. Other conventional and/or later developed wired and wireless networks may also be used.

The pharmacy benefit manager device 106 may be a device operated by an entity at least partially responsible for creation and/or management of the drug benefit plan. While the pharmacy benefit manager operating the pharmacy benefit manager device 106 is typically a PBM, or associated with a PBM, other entities may operate the pharmacy benefit manager device 106 on behalf of themselves, the PBM, or another entity.

In an example embodiment, some of the operations of the PBM that operates the pharmacy benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location. The pharmacy may then submit a claim to the PBM. The PBM may perform certain claim adjudication functions including verifying the eligibility of the member, reviewing the formulary to determine appropriate co-pay, coinsurance, and deductible for the prescription drug, and performing a drug utilization review (DUR) on the member prior to receiving the prescription for the member. If the PBM receives the prescription, the PBM may adjudicate the claim associated with the prescription drug and provide a response to the pharmacy following performance of adjudication functions for the received prescription. As part of the adjudication, the client (or the PBM on behalf of the client) may ultimately reimburse the pharmacy for filling the prescription drug when the prescription drug was successfully adjudicated.

In some embodiments, an application may be downloaded, installed, and launched on the member device 102 to enable the device operator to facilitate claim adjudication. The application may take advantage of hardware and/or software functionality provided by manufacturers of the member device 102 and/or developers of the operating system of the member device 102. For example, the application may use the SAFARI web browser on the IPHONE device, the Webkit browser on an ANDROID device, MOBILE INTERNET EXPLORER on a WINDOWS MOBILE device, or on any of the aforementioned devices. The application may include instructions that when executed on the member device 102, in the pharmacy benefit manager device 106, or healthcare provider device 108, cause a machine to change its state or perform tasks within the machine and with other machines.

The application may be downloaded to a healthcare provider device 108, the pharmacy benefit manager device 106, or member device 102. In some embodiments, the pharmacy benefit manager device 106 and/or the healthcare provider device 108 may be operated by an entity that makes available applications created by the application provider and/or third parties (e.g., the pharmacy benefit manager) for download and use on electronic devices. Examples of companies that operate the application provided by the pharmacy benefit manager device 106 may include Apple, Inc. through its operation of ITUNES STORE, Google, Inc. through its operation of ANDROID MARKET, AT&T through its operation of its APPCENTER, and Research In Motion Limited through its operation of BLACKBERRY APP WORLD. Each of these device companies cans host and supply proprietary apps, open apps, and apps by third parties. In some embodiments, the application may be downloaded from application download sites, the PBM, healthcare provider system, and/or a web-based application distribution system that may be accessed, e.g., via a web browser executed on an electronic device, such as the member device 102.

The member device 102 may be in a client-server relationship with the pharmacy benefit manager device 106 and/or the healthcare provider device 108, a peer-to-peer relationship with the pharmacy benefit manager device 106 and/or the healthcare provider device 108, or in a different type of relationship with the pharmacy benefit manager device 106 and/or the healthcare provider device 108.

The pharmacy benefit manager device 106 may be in communication directly (e.g., through local storage) and/or through the network 104 (e.g., in a cloud configuration or software as a service) with a database 110. The database 110 may store member data 112, claims data 114, and/or pharmacy data 116.

The member data 112 includes information regarding the members associated with the pharmacy benefit manager. Examples of the member data 112 include name, address, telephone number, e-mail address, prescription drug history, and the like. The member data 112 may include a client identifier that identifies the client associated with the member and/or a member identifier that identifies the member to the client. The member data 112 may include a universal identifier to identify claims associated with the member from one or more benefit plans. In some embodiments, the member data 112 may also include data regarding the benefit plan associated with the member and/or the client. The member data 112 may include an indication of authorization of whether a member has or is otherwise associated with a member device (e.g., the member device 102).

The claims data 114 includes information regarding the claims submitted by a pharmacy or the member to the pharmacy benefit manager. Examples of the claims data 114 may include data indicating eligibility for a prescription drug, access to the prescription drug, access to supporting information associated with the prescription drug, data associated with a provider of the prescription drug, demographic information associated with the member, data associated with a pharmacy dispensing the prescription drug, or any combination thereof.

The claims data 114 may be associated with a single benefit manager or multiple benefit managers. In some embodiments, the claims data 114 includes claims data for a member from a prior pharmacy benefit manager that is not the member's current pharmacy benefit manager.

The pharmacy data 116 may include information regarding pharmacies. The pharmacy data 116 may include, by way of example, location data regarding the location of the pharmacies, information data regarding the pharmacy hours and/or telephone number, pharmacy network association data defining the pharmacy network associations of which the pharmacies are associated, prescription drug availability, and the like.

While the system 100 in FIG. 1 is shown to include single devices 102, 106, 108, multiple devices may be used. The devices 102, 106, 108 may be the same type of device or may be different device types. When multiple devices are present, the multiple devices may be of the same device type or may be a different device type. Moreover, system 100 shows a single network 104; however, multiple networks can be used. The multiple networks may communicate in series with each other to link the devices 102, 106, 108 or in parallel to link the devices 102, 106, 108. In some embodiments, at least some of the functionality of the healthcare provider device 108 may be included in the pharmacy benefit manager device 106.

Figure 2:
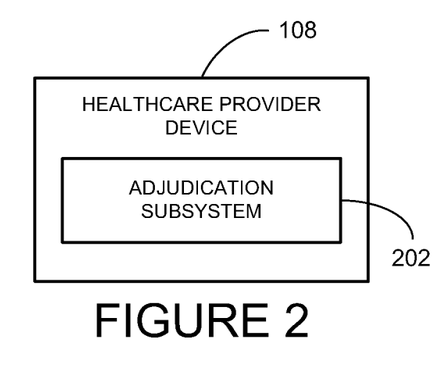
FIG. 2 is a block diagram of an example healthcare provider device that may be deployed within the system of FIG. 1, according to an example embodiment.

FIG. 2 illustrates the healthcare provider device 108, according to an example embodiment. The healthcare provider device 108 may be used by a healthcare provider operator prescribe a prescription drug for the member. The healthcare provider device 108 may be deployed in the system 100, or may otherwise be used.

The healthcare provider device 108 may include an adjudication subsystem 202. The adjudication subsystem 202 enables the device operator of the healthcare provider device 108 to adjudicate claims associated with prescription drugs.

Figure 3:
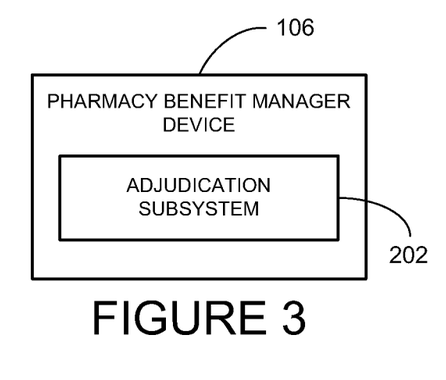
FIG. 3 is a block diagram of an example pharmacy benefit manager device that may be deployed within the system of FIG. 1, according to an example embodiment.

FIG. 3 illustrates the pharmacy benefit manager device 106, according to an example embodiment. The pharmacy benefit manager device 106 may be deployed in the system 100, or may otherwise be used.

The pharmacy benefit manager device 106 may include the adjudication subsystem 202. In some embodiments, the adjudication subsystem 202 may provide server-side functionality to the healthcare provider device 108. By way of example, the adjudication subsystem 202 may be deployed in both the healthcare provider device 108 and the pharmacy benefit manager device 106. The healthcare provider device 108 may then perform some of the functionality while other functionality is performed by the pharmacy benefit manager device 106.

Figure 4:
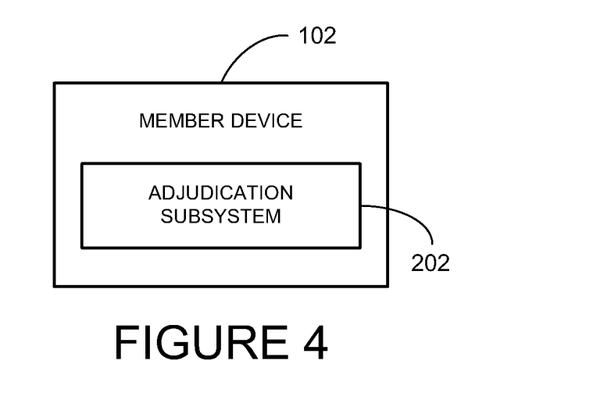
FIG. 4 is a block diagram of an example member device that may be deployed within the system of FIG. 1, according to an example embodiment.

FIG. 4 illustrates the member device 102, according to an example embodiment. The member device 102 may be deployed in the system 100, or may otherwise be used.

The member device 102 may include the adjudication subsystem 202. In some embodiments, the adjudication subsystem may provide server-side functionality to the healthcare provider device 108 and/or the pharmacy benefit manager device 106. By way of example, the adjudication subsystem 202 may be deployed in the healthcare provider device 108, the pharmacy benefit manager device 106, and the member device 102.

Figure 5:
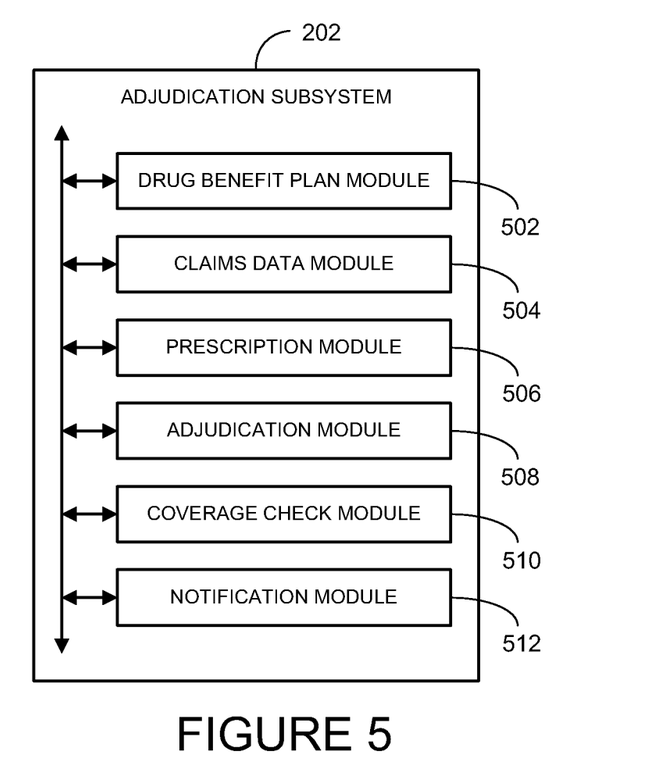
FIG. 5 is a block diagram of an example adjudication subsystem that may be deployed within the healthcare provider device of FIG. 2, the pharmacy benefit manager device of FIG. 3, or the member device of FIG. 4, according to an example embodiment.

FIG. 5 illustrates an example adjudication subsystem 202 that may be deployed in the member device 102, the pharmacy benefit manager device 106, the healthcare provider device 108, or otherwise deployed in another system. One or more modules are communicatively coupled and included in the adjudication subsystem 202 to enable claim adjudication. The modules of the adjudication subsystem 202 that may be included are the drug benefit plan module 502, the claims data module 504, the prescription module 506, the adjudication module 508, the coverage check module 510, and the notification module 512. Other modules may also be included.

In some embodiments, the modules of the adjudication subsystem 202 may be distributed so that some of the modules are deployed in the member device 102, some modules are deployed in the pharmacy benefit manager device 106, and some module are deployed in the healthcare provider device 108. In one embodiment, the modules are deployed in memory and executed by a processor coupled to the memory. The functionality contained within the modules 502-512 may be combined into a lesser number of modules, further divided among a greater number of modules, or redistributed among existing modules. Other configurations including the functionality of the modules 502-512 may be used.

The drug benefit plan module 502 may determine the status of a drug benefit plan of the member by determining whether the member has changed or is willing to change drug benefit plans. In some embodiments, the member may change benefit plans responsive to moving jobs or as a result of an employer of the member making changes to the benefit plans of the member. In some embodiments, the drug benefit plan module 502 may determine the status of a drug benefit plan of the member by receiving a response to an offer from the PBM to change benefit plans.

A claims data module 504 may access claims data associated with the member. In some embodiments, the claims data module 504 may access the database 110 to access member data 112, claims data 114, or pharmacy data 116. In some embodiments, the claims data module 504 may use a universal identifier associated with a member to access claims data from one or more databases 110 that may store claims data 114 associated with a member for different benefit plans. A member may have multiple benefit plans due to having multiple jobs, moving jobs, or obtaining additional and/or supplemental benefit plans via a different pharmacy benefit provider. In some embodiments, the claims data module 504 is able to access claims data associated with the member from one or more benefit plans using a universal identifier and additional identifying information of the member to verify the identity of the member. The universal identifier may be a unique identifier associated with a member. In some embodiments, the universal identifier may include but is not limited to numbers, letters, symbols, biometric information (e.g., fingerprints or facial recognition) or any combination thereof. A universal identifier may be similar to a social security number, in that it is unique to a member and may be assigned to the member by an entity or organization regardless of the provider of the benefit plan. Thus, if the member were to change benefit plans or otherwise changed information concerning their healthcare, a universal identifier may ensure that the history of the member may be accessed by healthcare providers to provide a thorough and comprehensive medical and prescription drug history.

The claims data module 504 may receive the pharmacy data 116. The pharmacy data 116 for all pharmacies, all pharmacies in pharmacy network associations of the client, all pharmacies in a particular network association, all pharmacies in pharmacy network associations of the client within a particular geographic area or within a particular geographic range from a starting point, or otherwise may be received. The pharmacy data 116 may be received periodically by the claims data module 504 on the pharmacy benefit manager device 106.

A prescription module 506 may identify a current-filled prescription based on the claims data. In some embodiments, the prescription module 506 may use the claims data accessed by the claims data module 504 to identify a current-filled prescription of a member. In some embodiments, a current-filled prescription of a member is an existing prescription of a prescription drug for the member which the member has recently had the prescription filled.

An adjudication module 508 may perform at least one adjudication operation for the current filled prescription prior to receiving a new request for the current filled prescription. In some embodiments, the adjudication module 508 may perform one or more operations for the current-filled prescription. The adjudication module 508 may perform an adjudication operation for the current-filled prescription prior to receiving a new request for the current-filled prescription. In some embodiments, the adjudication module 508 may determine the price of the prescription drug of the current-filled prescription for one or more pharmacies capable of fulfilling the prescription. In some embodiments, the adjudication module 508 may identify possible side effects of the prescription drug. The adjudication module 508 may identify possible alternative prescription drugs, such as those in the same therapy class, but different manufacturer or those in different therapy classes. The adjudication module 508 may execute an adjudication task prior to receipt of a current prescription being received for adjudication. A single adjudication task or multiple adjudication tasks may be executed.

A coverage check module 510 may determine the new request is fillable based on the performance of at least one adjudication operation by the adjudication module 508. In some embodiments, the coverage check module 510 uses the results of the adjudication operations performed by the adjudication module 508 to determine whether the request is fillable by the pharmacist associated with the PBM. In some embodiments, the determination is directed at whether a future request on the prescription would be fillable, if/when the request is made. In some embodiments, the determination may be based on the results of the adjudication operations, availability of the prescription drug at an identified pharmacy (retail or mail order), and benefits available to the member under the drug benefit plan.

A notification module 512 may generate a notification to the member based on the determination. In some embodiments, the notification module 512 may generate an email, text message, voice message, letter, or other type of communication. The notification may be a summary of the determination whether the request is fillable. In some embodiments, the notification may contain a detailed description regarding the factors that may have influenced the determination. In some embodiments, the notification may be a message to the pharmacy benefit manager to speak with a care coordinator. The care coordinator may provide details to the member regarding the determination as well as outline steps to move forward with switching a pharmaceutical delivery channel for the prescription drug or to terminate the process of switching the pharmaceutical delivery channel.

Figure 6:
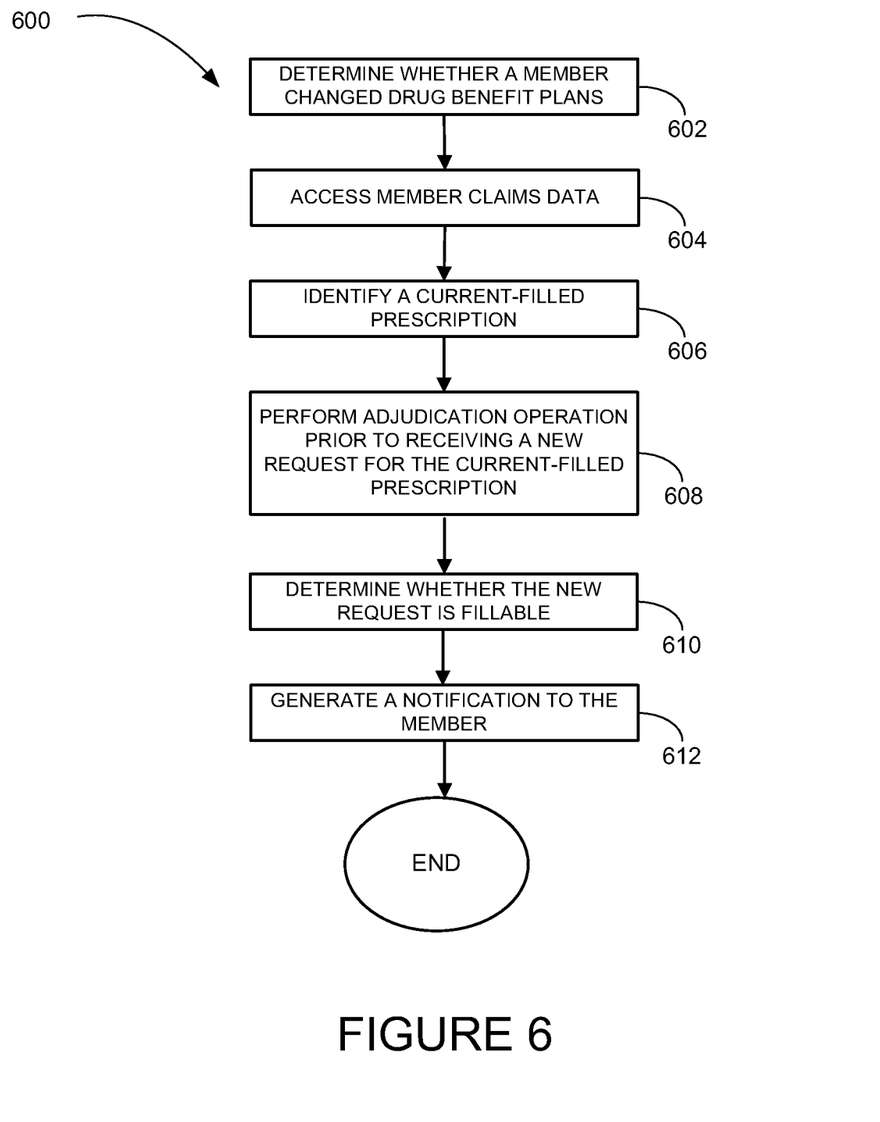
FIG. 6 is a block diagram of a flowchart illustrating methods for claim adjudication, according to an example embodiment.

FIG. 6 illustrates a method 600 for claim adjudication, according to an example embodiment. The method 600 may be performed by the pharmacy benefit manager device 106, partially by the pharmacy benefit manager device 106 and partially by the member device 102 and/or the healthcare provider device 108, or may be otherwise performed.

A determination as to whether a member changed drug benefit plans may be made at block 602. In some embodiments, the adjudication subsystem 202 may receive a status of a drug benefit plan associated with a member. The status of a drug benefit plan may be determined by the adjudication subsystem 202 by querying the database 108 or other knowledge base using identifying information associated with the member. In some embodiments, the adjudication subsystem 202 may receive an indication that the member intends to change drug benefit plans. The indication may be received from the member, an employer of the member, or some entity associated with the member with knowledge of a change in benefit plans (e.g., the HR department of the employer of a member may indicate that the company will be changing benefit plans). In some embodiments, the indication may be in the form of an acceptance to an offer from the pharmacy benefit manager or pharmacy to the member, incentivizing the member to switch benefit plans.

Member claims data 112 may be accessed at block 604. In some embodiments, claims data associated with a member may be stored by the pharmacy benefit manager in a database 108, may be a database or other storage means accessed by the PBM, or may be received from a different entity, such as a pharmacy. In some embodiments, claims data may include data indicating eligibility for a prescription drug, access to the prescription drug, access to supporting information associated with the prescription drug, data associated with a provider of the prescription drug, demographic information associated with the member, data associated with a pharmacy dispensing the prescription drug, data indicating whether prior authorization is required before dispensing the prescribed drug in ensure the drug is being used for a medically-approved indication, or any combination thereof.

In some embodiments, claims data may be accessed using a universal identifier associated with the member. By using a universal identifier associated with the member, historic claims data may be accessed despite changes in benefit plans or other obstacles, in order to compile a more comprehensive claims profile for the member. For example, assume a member was employed by company A and then switched to company B. Without a universal identifier, a PBM may only be able to access information for the member from company A or company B, but not both. Thus, the PBM could not compile a complete profile for the member, which may lead to inefficiencies and may degrade the quality of care received by the member. However, using the universal identifier, the PBM could access all information associated with the universal identifier, regardless of the benefit program associated with a single employer, thus enabling and ensuring an accurate compilation of data associated with a member. Thus, the adjudication subsystem 202 may access claims data using a universal identifier associated with a member to generate a claims history of the member using claims data from one or more drug benefit programs. In some embodiments, a claims history may be compiled and/or generated using claims data received from the one or more pharmacies that may have fulfilled the prescribed drug, the prescribing healthcare provider, and/or the member.

In some embodiments, the claims data received from different sources, such as different drug benefit programs, may be analyzed to better identify data points for easier data integration. For example, and in furtherance of the example from above, if the member started using drug X while under a drug benefit program provided by company A on Dec. 12, 2011 but had previously starting using drug X on Jul. 13, 2011 while at company B, under a different benefit plan, both Jul. 13, 2011 and Dec. 12, 2011 may be identified as first-fill dates, or the dates on which a prescription for the drug X was first filled for the member. The analysis of claims data received from different sources, e.g., based on the universal identifier, may identify the two dates and determine that Jul. 13, 2011 was the first date the member started taking drug X and therefore is the correct overall first-fill date. When integrating data received for the member from a benefit program under company A and a different benefit program under company B, the adjudication subsystem may identify Jul. 13, 2011 as the first-fill date and determine that Dec. 12, 2011 should not be maintained as the first-fill date in the comprehensive claims history for the member. Thus, in some embodiments, analyzing the claims data from multiple drug benefit programs and combining the claims data from the drug benefit programs in response to the analysis to generate the claims history of the member may not only increase efficiency but also enhance accuracy to provide better care to the member.

In some embodiments, the adjudication subsystem may receive a prescription drug history of the member from the member. The adjudication subsystem may receive the prescription drug history of the member via a web interface or a user interface of a client application. In an example, the member may enter data and member history using the member device 102. The member may provide information to the adjudication subsystem by entering data associated with any prescription drugs the member may have taken or used in the past or is currently taking. The prescription drug history may be used to supplement the claims data received from the benefit programs or may be used in lieu of the claims data, especially if the claims data from the benefits programs is not available for use by the adjudication subsystem. In some embodiments, one or more adjudication operations may be performed based on the received prescription drug history of the member.

A current-filled prescription may be identified at block 606. A current-filled prescription of a member may be an existing prescription drug prescribed to the member and already filled by a pharmacy, either retail or member. The current-filled prescription of the member may be identified using the claims data of the member.

One or more adjudication operations may be performed prior to receiving a new request for the current-filled prescription at block 608. In some embodiments, the adjudication subsystem 202 may perform one or more operations for the current-filled prescription. In some embodiments, the adjudication subsystem may perform at least one adjudication operation for the current-filled prescription prior to receiving a new request for the current-filled prescription. A new request for the current-filled prescription of a member may be an indication from the member for switching their pharmaceutical delivery channel (e.g., switching from retail purchase of the prescription drugs to mail-order delivery of the prescription drugs) for the current-filled prescription. In some embodiments, the indication may be responsive to an offer sent to the member during a patient outreach or therapy outreach.

In some embodiments, the adjudication operation may include determining the price of the prescription drug of the current-filled prescription for one or more pharmacies capable of fulfilling the prescription. In some embodiments, prices for the prescription drug may be determined only for pharmacies that are within an identified pharmacy network. In some embodiments, prices for the prescription drug may be determined for pharmacies within an identified geographic area. In some embodiments, prices for the prescription drug may be determined for pharmacies identified using other criteria.

In some embodiments, the adjudication operation may include identifying possible side effects of the prescription drug. The adjudication operation may include identifying possible alternative prescription drugs, such as those in the same therapy class, but different manufacturer (e.g., identifying generic drugs when prescribed a brand drug and vice versa). The adjudication operation may include identifying possible alternative prescription drugs, such as those in different therapy classes. The adjudication subsystem may also identify possible side effects of the alternative prescription drugs as well as any indication of possible side effects resulting from a mixture of the prescription drug and other prescription and/or non-prescription drugs taken by the member. In some embodiments, identifying the other prescription and/or non-prescription drugs taken by the member may be another adjudication operation of the adjudication subsystem. In some embodiments, the price of the prescribed drug at each of the pharmacies capable of fulfilling the prescription may be transmitted to the member.

In some embodiments, the adjudication operation may include ranking or rating the one or more pharmacies capable of filling the current-filled prescription of the member. In some embodiments, the ranking or rating generated by the adjudication subsystem may be based on pharmacy data, pricing data, member feedback, or other criteria. The ranking and/or rating generated by the adjudication subsystem 202 may be sortable or otherwise manipulated by the member to identify a pharmacy that may meet the specific needs of the member based on the criteria provided by the member.

A determination as to whether the new request is fillable may be made at block 610. In some embodiments, the determination that the new request is fillable may be based on the performance of one or more adjudication operations. In some embodiments, the determination may indicate that prescription is not fillable by a pharmacy due to availability of the prescription drug at the pharmacy. In some embodiments, the determination may indicate the prescription is not fillable because drug benefit plan of the member may not cover the cost of the prescription drug.

A notification to the member may be generated at block 612. In some embodiments, a notification to the member may be generated based on the determination as to whether the new request is fillable. In some embodiments, the notification can be a phone call, text message, email message, web-message, letter, or other type of communication to the member. The notification to the member may include the results of the claim adjudication operations. For example, if during the claim adjudication operations, it is determined that the prescription drug may negatively interact with a drug the member is currently taking, the member may be notified through a notification which may outline the issue and may indicate that the member contact their physician or pharmacist. In some embodiments, the claim adjudication operation may indicate that switching pharmaceutical delivery channels (e.g., from retail delivery of a prescription drug to a mail-order delivery of the prescription drug) would pose no problems and include the next steps in the process to switch pharmaceutical delivery channels. In some embodiments, the notification may include advising the member that a prior authorization is needed to continue with the prescription drug associated with the member's last fill. In some embodiments, the notification may include notifying the member that the prescription drug associated with the member's last fill is covered at a different rate or not covered. In some embodiments, the notification may include notifying the member that a different prescription drug is a preferred or more preferred drug according to a formulary associated with the client of the member. Other types of notifications may be provided.

In some embodiments, the method 600 may be performed prior to the member submitting a request for a refill of an associated prescription drug and/or a claim being submitted to the pharmacy benefit manager for the associated prescription drug.

Figure 7:
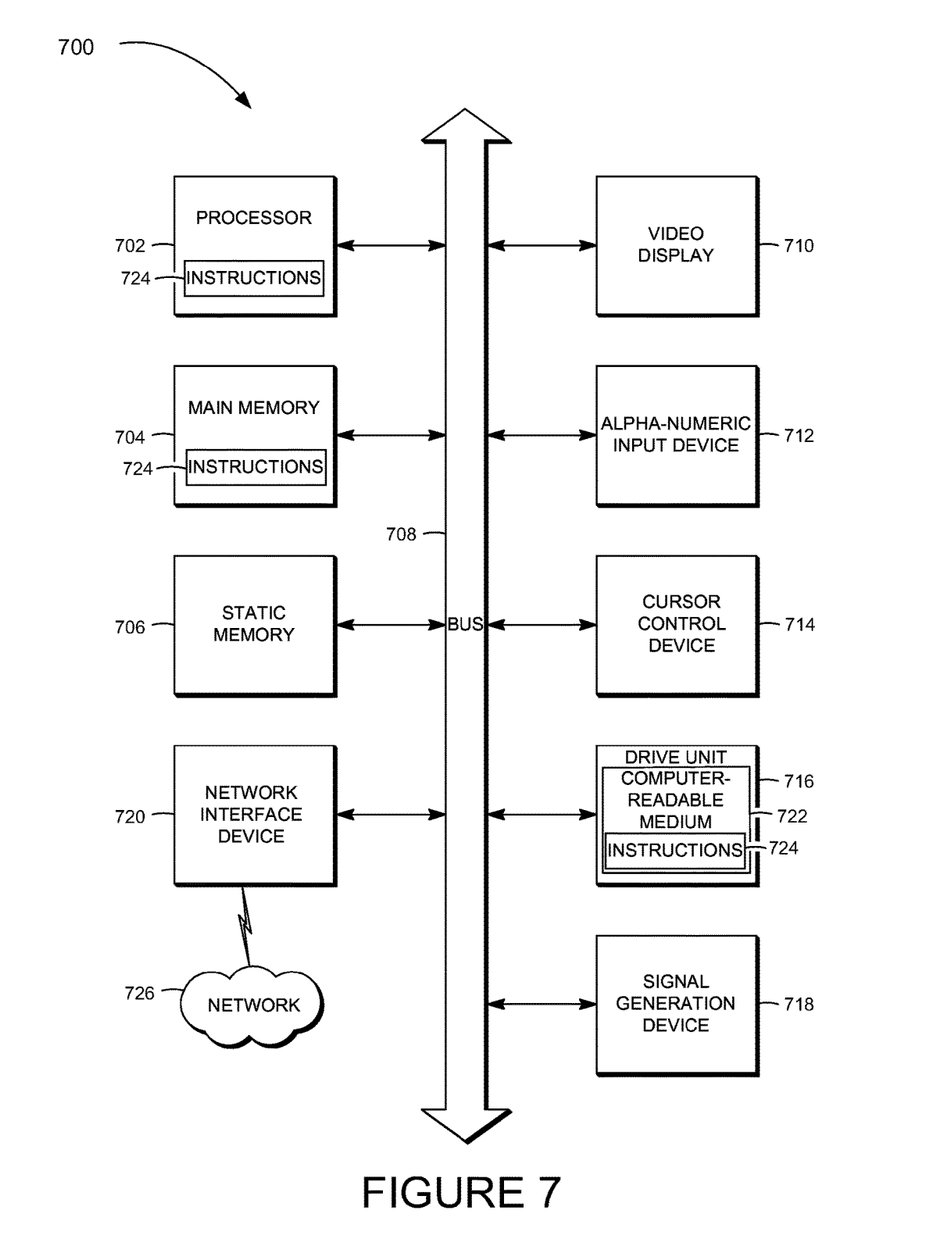
FIG. 7 is a block diagram of a machine in the example form of a computer system within which a set of instructions for causing the machine to perform any one or more of the methodologies discussed herein may be executed or stored.

FIG. 7 shows a block diagram of a machine in the example form of a computer system 700 within which a set of instructions may be executed causing the machine to perform any one or more of the methods, processes, operations, or methodologies discussed herein. The mobile electronic device 102, the network manager device 106, and/or the application provider device 108 may include the functionality of the one or more computer systems 700.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 712 (e.g., a central processing unit (CPU) a graphics processing unit (GPU) or both), a main memory 704 and a static memory 706, which communicate with each other via a bus 708. The processor 712 may include a single discrete electronic processing element or a multiple electronic processing elements that can execute the processes, flows, and methods described herein.

The computer system 700 further includes a video display unit 710 (e.g., a liquid crystal display (LCD) or a cathode ray tube (CRT)). The computer system 700 also includes an alphanumeric input device 712 (e.g., a keyboard), a cursor control device 714 (e.g., a mouse), a drive unit 716, a signal generation device 718 (e.g., a speaker) and a network interface device 720.

The drive unit 716 includes a computer-readable medium 722 on which is stored one or more sets of instructions (e.g., software 724) embodying any one or more of the methodologies or functions described herein. The software 724 may also reside, completely or at least partially, within the main memory 704 and/or within the processor 712 during execution thereof by the computer system 700, the main memory 704 and the processor 712, also constituting computer-readable media.

The software 724 may further be transmitted or received over a network 726 via the network interface device 720.

While the computer-readable medium 722 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a status of a drug benefit plan associated with a member may be determined. Claims data associated with the member may be accessed. A current-filled prescription may be identified based on the claims data. At least one adjudication operation for the current-filled prescription may be performed prior to receiving a new request for the current-filled prescription. The new request may be determined as fillable based on the performance of the at least one adjudication operation. A notification may be generated to the member based on the determination.

In an example embodiment, a system may include a processor and a memory coupled to the processor. A drug benefit plan module deployed in the memory and executed by the processor to determine a status of a drug benefit plan associated with a member. A claims data module deployed in the memory and executed by the processor to access claims data associated with the member. A prescription module deployed in the memory and executed by the processor to identify a current-filled prescription based on the claims data. An adjudication module deployed in the memory and executed by the processor to perform at least one adjudication operation for the current filled prescription prior to receiving a new request for the current filled prescription. A coverage check module deployed in the memory and executed by the processor to determine the new request is fillable based on the performance; and a notification module deployed in the memory and executed by the processor to generate a notification to the member based on the determination.

Thus, methods and systems for claim adjudication have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A method comprising:

determining, on a processor of an adjudication subsystem of a pharmacy benefit manager device, a status reflecting that a member, having a universal identifier, has changed from a drug benefit plan to a different drug benefit plan;

associating, on the processor of the adjudication subsystem of the pharmacy benefit manager device, the different drug benefit plan with the universal identifier;

accessing, on the processor of the pharmacy benefit manager device, first claims data associated with the drug benefit plan based on the universal identifier associated with the member from a database via a network;

determining, on the processor of the pharmacy benefit manager device, that second claims data is also associated with the universal identifier;

accessing, on the processor of the pharmacy benefit manager device, the second claims data associated with the different drug benefit plan based on the universal identifier associated with the member from the database via the network;

analyzing, on the processor of the pharmacy benefit manager device, the first claims data from the drug benefit plan and the second claims data from the different drug benefit plan;

combining, on the processor of the pharmacy benefit manager device, the first claims data from the drug benefit plan and the second claims data from the different drug benefit plan in response to analysis of the first claims data and the second claims data to generate a claims history of the member;

identifying, on the processor of the pharmacy benefit manager device, a current-filled prescription based on the first claims data from the drug benefit plan accessed using the universal identifier and the second claims data from the different drug benefit plan accessed using the universal identifier;

performing, on the processor of the pharmacy benefit manager device, at least one adjudication operation for the current-filled prescription prior to receiving a new request for the current-filled prescription from a pharmacy device via a network, wherein performing the at least one adjudication operation for the current-filled prescription comprises determining a co-pay, coinsurance, and deductible for the current-filled prescription at each of one or more pharmacies capable of fulfilling the current-filled prescription;

prior to receipt of the new request for the current-filled prescription, determining, on the processor of the pharmacy benefit manager device, whether the new request is fillable subsequent to and based on performance of the at least one adjudication operation;

generating, on the processor of the pharmacy benefit manager device, a notification to the member based on a result of a determination of whether the new request is fillable;

transmitting the notification from a network interface device of the pharmacy benefit manager device to a member device of the member via the network; and dispensing the current-filled prescription at a pharmacy of the one or more pharmacies capable of fulfilling the current-filled prescription when the new request is fillable.

2. The method of claim 1, wherein the first claims data includes data indicating eligibility for a prescription drug, access to the prescription drug, access to supporting information associated with the prescription drug, data associated with a provider of the prescription drug, demographic information associated with the member, data associated with the pharmacy dispensing the prescription drug, or any combination thereof.

3. The method of claim 1, further comprising:

generating the claims history of the member based on the first claims data from the drug benefit plan and the second claims data from the different drug benefit plan; and performing the at least one adjudication operation based on the generated claims history of the member.

4. The method of claim 3, wherein the different drug benefit plan is related to at least one of a current job, a supplemental benefit, or both, the drug benefit plan being related to a prior job, wherein the first claims data from the drug benefit plan and the second claims data from the different drug benefit plan are linked by the universal identifier;

wherein combining the first claims data and the second claims data includes:

determining a first-fill date for a prescription drug associated with the universal identifier from both the drug benefit plan and the different drug benefit plan, and identifying potential interactions between a first drug filled under the drug benefit plan and a second drug filled under the different drug benefit plan.

5. The method of claim 1, further comprising:

receiving a prescription drug history of the member from the member; and performing the at least one adjudication operation based on receipt of the prescription drug history of the member.

6. The method of claim 1, wherein performing the at least one adjudication operation for the current-filled prescription further comprises:

determining a price of the current-filled prescription at each of one or more pharmacies capable of fulfilling the current-filled prescription; and transmitting to the member the price of the current-filled prescription at each of the one or more pharmacies capable of fulfilling the current-filled prescription.

7. A non-transitory machine-readable medium comprising instructions, which when executed by one or more processors, cause the one or more processors to perform the following operations:

determine a status reflecting that a member, having a universal identifier, has changed from a drug benefit plan to a different drug benefit plan;

associate the different drug benefit plan with the universal identifier;

access first claims data associated with drug benefit plan based on the universal identifier associated with the member from a database via a network;

determine that second claims data is also associated with the universal identifier;

access the second claims data associated with the different drug benefit plan based on the universal identifier associated with the member from the database via the network;

analyze the first claims data from the drug benefit plan and the second claims data from the different drug benefit plan;

combine the first claims data from the drug benefit plan and the second claims data from the different drug benefit plan in response to analysis of the first claims data and the second claims data to generate a claims history of the member;

identify a current-filled prescription based on the first claims data accessed using the universal identifier from the drug benefit plan and the second claims data from the different drug benefit plan accessed using the universal identifier;

perform at least one adjudication operation for the current-filled prescription prior to receiving a new request for the current-filled prescription from a pharmacy device via a network, wherein instructions to perform the at least one adjudication operation for the current-filled prescription comprise instructions to determine a co-pay, coinsurance, and deductible for the current-filled prescription at each of one or more pharmacies capable of fulfilling the prescription;

prior to receipt of the new request for the current-filled prescription, determine whether the new request is fillable based on performance of the at least one adjudication operation for the current-filled prescription;

generate a notification to the member based on a result of a determination of whether the new request is fillable;

transmit the notification to a member device of the member via the network; and cause the current-filled prescription to be dispensed at a pharmacy of the one or more pharmacies capable of fulfilling the current-filled prescription when the new request is fillable.

8. The non-transitory machine-readable medium of claim 7, wherein the first claims data includes data indicating eligibility for a prescription drug, access to the prescription drug, access to supporting information associated with the prescription drug, data associated with a provider of the prescription drug, demographic information associated with the member, data associated with the pharmacy dispensing the prescription drug, or any combination thereof.

9. The non-transitory machine-readable medium of claim 7, further comprises instructions to:
receive a prescription drug history of the member from the member; and
perform the at least one adjudication operation based on the received prescription drug history of the member.

10. The non-transitory machine-readable medium of claim 7, wherein instructions to perform the at least one adjudication operation for the current-filled prescription comprise instructions to:
determine a price of the current-filled prescription at each of one or more pharmacies capable of fulfilling the current-filled prescription; and
transmit the price of the current-filled prescription at each of the one or more pharmacies capable of fulfilling the prescription.

11. A system comprising:
a processor and a memory coupled to the processor;
a drug benefit plan module deployed in the memory and executed by the processor of an adjudication subsystem of a pharmacy benefit manager device to determine a status reflecting that a member, having a universal identifier, has changed from a drug benefit plan to a different drug benefit plan and associate the different drug benefit plan with the universal identifier;
a claims data module deployed in the memory and executed by the processor of the pharmacy benefit manager device to access first claims data associated with the drug benefit plan based on the universal identifier associated with the member from a database via a network, determine that second claims data is also associated with the universal identifier, access the second claims data associated with the different drug benefit plan based on the universal identifier associated with the member from the database via the network, analyze the first claims data from the drug benefit plan and the second claims data from the different drug benefit plan, combine the first claims data from the drug benefit plan and the second claims data from the different drug benefit plan in response to analysis of the first claims data and the second claims data to generate a claims history of the member;
a prescription module deployed in the memory and executed by the processor of the pharmacy benefit manager device to identify a current-filled prescription based on the first claims data accessed using the universal identifier from the drug benefit plan and the second claims data from the different drug benefit plan accessed using the universal identifier;
an adjudication module deployed in the memory and executed by the processor of the pharmacy benefit manager device to perform at least one adjudication operation for the current-filled prescription prior to receiving a new request for the current-filled prescription from a pharmacy device via a network, wherein the adjudication module performing the at least one adjudication operation comprises that adjudication module determining a co-pay, coinsurance, and deductible for the current-filled prescription at each of one or more pharmacies capable of fulfilling the prescription;
a coverage check module deployed in the memory and executed by the processor of the pharmacy benefit manager device to determine, prior to receipt of the new request for the current-filled prescription, that the new request is fillable based on performance of the at least one adjudication operation, and cause the current-filled prescription to be dispensed at a pharmacy of the one or more pharmacies capable of fulfilling the current-filled prescription when the new request is fillable;
a notification module deployed in the memory and executed by the processor of the pharmacy benefit manager device to generate a notification to the member based on a result of a determination of whether the new request is fillable; and
a network interface device of the pharmacy benefit manager device in communication with a network to transmit the notification to a member device of the member via the network.

12. The method of claim 1, wherein the status reflects that the member has changed from the drug benefit plan to the different drug benefit plan since previously receiving a prescription drug fill of the current-filled prescription, the prescription drug fill being adjudicated under the drug benefit plan.

13. The method of claim 1, wherein the status reflects an acknowledged willingness that the member has changed from the drug benefit plan to the different drug benefit plan since previously receiving a prescription drug fill of the current-filled prescription, the prescription drug fill being adjudicated under the drug benefit plan.

14. The method of claim 1, wherein the at least one adjudication operation includes determining coverage of the current-filled prescription under the drug benefit plan.

15. The method of claim 1, wherein the notification reflects that the current-filled prescription is not fillable under the different drug benefit plan.

16. The method of claim 1, wherein the determination of the status reflects that the member has changed from the drug benefit plan to the different drug benefit plan, the current-filled prescription being associated with the drug benefit plan, and wherein performance of the at least one adjudication operation is based on a determination that the status that the member has changed from the drug benefit plan to the different drug benefit plan.

17. The method of claim 1, wherein the status is a drug benefit enrollment status reflecting drug benefit plan enrollment, change of the drug benefit enrollment status reflecting member changes of drug benefit plan enrollment from the drug benefit plan to the different drug benefit plan.

18. The method of claim 1, wherein the determination of the status reflects that the member will change from the drug benefit plan to the different drug benefit plan, the current-filled prescription being associated with the drug benefit plan, and wherein performance of the at least one adjudication operation is based on a determination that the status of the member will change from the drug benefit plan to the different drug benefit plan.

19. The method of claim 1, wherein performing the at least one adjudication operation includes determining that the new request for the current-filled prescription requires a prior authorization, and wherein a determination of whether the new request is fillable subsequent to and based on performance of the at least one adjudication operation includes determining that the current-filled prescription did not require a prior authorization, and the notification reflects that the member needs to obtain a prior authorization in conjunction with receiving the new request for the current-filled prescription.

* * * * *